United States Patent [19]

Markowitz

[11] Patent Number: 5,103,820
[45] Date of Patent: Apr. 14, 1992

[54] VDD PACEMAKER WITH SELECTABLE POST-VENTRICULAR ATRIAL REFRACTORY PERIODS

[75] Inventor: H. Toby Markowitz, Roseville, Minn.

[73] Assignee: Medtronic, Inc., Minneapolis, Minn.

[21] Appl. No.: 567,431

[22] Filed: Aug. 14, 1990

[51] Int. Cl.⁵ .............................................. A61N 1/368
[52] U.S. Cl. ........................................... 128/419 OPG
[58] Field of Search .................................. 128/419 PG

[56] References Cited

U.S. PATENT DOCUMENTS

| | | | |
|---|---|---|---|
| 3,648,702 | 3/1972 | Greatbutch | 128/419 P |
| 4,059,116 | 11/1977 | Adams | 128/419 PG |
| 4,304,328 | 12/1981 | Fischer | 128/419 PG |
| 4,344,437 | 8/1982 | Markowitz | 128/419 PG |
| 4,363,325 | 12/1982 | Koline et al. | 128/419 PG |
| 4,407,287 | 10/1983 | Herpers | 28/419 PG |
| 4,428,378 | 1/1984 | Anderson et al. | 128/419 PG |
| 4,467,807 | 8/1984 | Bornzin | 128/419 PG |
| 4,515,161 | 5/1985 | Wittkampf et al. | 128/419 PG |
| 4,539,991 | 9/1985 | Boute et al. | 128/419 PG |
| 4,554,920 | 11/1985 | Baker, Jr. et al. | 128/419 PG |
| 4,554,921 | 11/1985 | Boute et al. | 128/419 PG |
| 4,712,556 | 12/1987 | Baker, Jr. | 128/419 PG |
| 4,890,617 | 1/1990 | Markowitz et al. | 128/419 PG |
| 4,920,965 | 5/1990 | Funke et al. | 128/419 PG |

OTHER PUBLICATIONS

Rate Responsive Dual Chamber Facing.
"Model 2409 Programmable, Atrial Synchronous Ventricular Inhibited Pulse Generator", Technical Manual, Mar. 1981 by Medtronic, Inc.

*Primary Examiner*—William E. Kamm
*Assistant Examiner*—Kennedy J. Schaetzle
*Attorney, Agent, or Firm*—Reed A. Duthler

[57] ABSTRACT

An improved atrial synchronous, dual-chamber pacemaker provided with a variable refractory period during which the pacemaker is not responsive to sensed atrial contractions. The atrial refractory period is selected based upon whether the ventricular pacing pulse preceding the refractory period occurred as a result of time out of the interval corresponding to the basic ventricular pacing rate or due to the time out of the A-V delay interval initiated in response to sensing of a natural atrial contraction.

7 Claims, 5 Drawing Sheets

VDD PACEMAKER WITH SELECTABLE POST-VENTRICULAR ATRIAL REFRACTORY PERIODS

BACKGROUND OF THE INVENTION

This invention pertains generally to the field of electrical heart pacemakers and control circuits therefor and more specifically to pacemakers which are adapted to operate in the atrial synchronous mode generally referred to as "VDD".

VDD pacemakers are first disclosed in U.S. Pat. No. 3,648,707 issued to Wilson Greatbatch, on Mar. 14, 1972, incorporated herein by reference in its entirety. This pacemaker included electrodes for sensing contractions of the atrium and ventricles, and a pulse generator for pacing the ventricle. After sensing a contraction of the ventricle or pacing the ventricle, a lower rate timer was restarted. If this timer expired, it triggered generation of a ventricular pacing pulse. Also included was an A-V interval timer, initiated in response to the sensing of an atrial contraction. On expiration of the A-V interval, a ventricular pacing pulse would also be triggered. The pacemaker included an upper rate timer, initiated following ventricular pacing or sensing of a ventricular contraction. During the upper rate interval, time out of the A-V interval timer would not be effective to trigger a ventricular pacing pulse. The upper rate timer allowed for inhibition of the ventricular pulse generator in the event that a natural ventricular contraction followed the sensed atrial contraction and also defined a maximum synchronous pacing rate. In other words, the pacemaker would only pace the ventricle in synchrony to the atrium up to a predetermined rate, corresponding to the upper rate interval. If the atrial rate exceeded this rate, the pacing rate would fall to ½ of the sensed atrial rate or to the lower rate, whichever was higher.

U.S. Pat. No. 4,059,116 issued to Adams on Jan. 12, 1976, also incorporated herein by reference in its entirety, included an improvement to the pacemaker disclosed in Greatbatch. In the Adams pacemaker, rather than blocking a ventricular stimulus in response to time out of the A-V interval during the upper rate interval, generation of a stimulus pulse was delayed until the end of the upper rate interval. In addition, a post-ventricular atrial refractory period was included, which specified a period of time following a ventricular pacing pulse or a sensed ventricular contraction, during which an atrial contraction would not be sensed. The net result of these two additional features was to produce a pacemaker which did not display such an abrupt drop in average ventricular pacing rate in response to a natural atrial rate which exceeded the rate defined by the upper rate interval. Instead, the interval between sensed atrial contractions and ventricular pacing pulses was gradually lengthened, until an atrial contraction fell within the post-ventricular atrial refractory period. The pacemaker would resynchronize on the next subsequent atrial contraction. The behavior of the Adams pacemaker resembled the natural physiologic condition known as Wenckebach syndrome. In commercially marketed pacemakers employing the Adams invention, the behavior of the pacemaker in the presence of high natural atrial rates is referred to as "Psuedo-Wenckebach" or "Pacemaker-Wenckebach" upper rate behavior.

In some heart patients, an ectopic ventricular contraction or a paced ventricular contraction not preceded by an atrial contraction may give rise to reverse conduction, back to the atrium. This is typically known as "retrograde conduction" and may produce an atrial contraction. This electrical signal accompanying such a contraction is typically referred to as a "retrograde P-wave". Retrograde P-waves typically occur within 100 to 400 ms following an ectopic ventricular contraction. If the post-ventricular atrial refractory period of the device is short enough, a retrograde P-wave may be sensed and initiate timing of the A-V interval by the pacemaker, causing generation of a subsequent ventricular pacing pulse at the expiration of the upper rate interval. If the interval between retrograde atrial depolarization and the subsequent ventricular pacing pulse is lengthy, a subsequent retrograde P-wave may be generated, reinitiating the cycle. This behavior, when it persists, is referred to as "pacemaker mediated tachycardia". Numerous improvements and modifications to dual chamber pacemakers have been suggested in order to avoid this problem.

Perhaps the simplest solution to this problem has been the provision of a lengthy post-ventricular atrial refractory period. However, the maximum tracking rate of an atrial synchronous pacemaker is limited to the rate corresponding to the post-ventricular refractory period plus the A-V interval. A 400 ms post-ventricular atrial refractory period, for example, in conjunction with a 100 ms A-V delay, would allow the pacemaker to track atrial rates only up to 120 bpm (500 ms.). In many cases, it is believed desirable to allow the pacemaker to track much higher natural atrial rates and use longer AV intervals. For example up to rates in excess of 150 bpm and AV intervals up to 200 ms. Simple lengthening of the post-ventricular atrial refractory period thus does not provide a universally acceptable solution to the problem of pacemaker mediated tachycardia.

In the context of DDD type pacemakers, a commonly employed feature directed towards eliminating pacemaker mediated tachycardia has been the lengthening of the post-ventricular atrial refractory period following a sensed natural contraction not preceded by an atrial contraction. This approach is disclosed in U.S. Pat. No. 4,407,287, issued to Herpers on Oct. 4, 1983, also incorporated herein by reference in its entirety.

In a DDD pacemaker, as disclosed in Herpers, all paced ventricular contractions are preceded by atrial contractions, either sensed or paced. However, in the context of a VDD pacemaker, another problem arises which does not display itself in the context of a DDD pacemaker. When atrial rates drop below the ventricular pacing rate set by the lower rate timer in a VDD pacemaker, the ventricular pulse generator generates pacing pulses, asynchronous to the atrium. After several pacing pulses, one pulse may be closely followed by the next subsequent bradycardic atrial contraction, which will initiate the A-V interval, and cause generation of a second, closely spaced ventricular pacing pulse at the expiration of the upper rate interval. This may initiate a pacemaker-mediated tachycardia, as discussed above.

One approach to solving this problem in the context of a VDD pacemaker is set forth in U.S. Pat. No. 4,363,325, issued to Roline et al on Dec. 14, 1982. In this case, if the atrial rate drops below a preset rate, the device switches to ventricular inhibited pacing at a second, higher rate. Returning to atrial synchronous (VDD) pacing is delayed until two successive atrial contractions at a rate higher than the ventricular inhibited rate are detected. This approach avoids the generation of closely spaced ventricular pacing pulses discussed above. However, switching to a ventricular inhibited mode prevents the pacemaker from deriving any benefit from synchronous pacing, while in VVI mode.

U.S. Pat. No. 4,344,437 issued to Markowitz on Aug. 17, 1982, represents an alternative approach to prevention of closely spaced ventricular pacing pulses in VDD pacemakers. In this device, in response to generation of a pacing pulse due to time out of the lower rate timer, the upper rate interval of the pacemaker is lengthened. This prevents an atrial bradycardia from resulting in too closely spaced ventricular pacing pulses in VDD mode. However, this approach to the problem does not address the related problem of retrograde P-waves, discussed above.

In the context of DDD pacemakers, a variety of proposals have been made to vary the post-ventricular atrial refractory period in complex fashion depending upon sensed atrial rate and sensed timing of occurrences of atrial contractions, as disclosed in U.S. Pat. No. 4,920,965 issued May 1, 1990 for a "Dual Chamber Pacemaker With Adaptive Atrial Escape Interval" and in U.S. Pat. Nos. 4,554,921 and 4,503,857 issued to Boute et al. These microprocessor based pacemakers include programs which provide for recalculation of post-ventricular atrial refractory periods, in complex fashion, based upon the above measured parameters. While these devices are believed to provide substantial useful advantages to prior art DDD pacemakers, monitoring and follow-up of the pacemakers requires telemetry of diagnostic markers to allow for determination of proper functioning.

SUMMARY OF THE INVENTION

The present invention is a VDD pacemaker of the type generally described in the above-cited Greatbatch and Adams patents. It includes a lower rate timer which defines a V-V interval extending from a sensed ventricular contraction or the delivery of a ventricular pacing pulse and which, on expiration, causes the generation of a ventricular pacing pulse. It includes an A-V delay timer which times out an A-V interval initiated in response to sensing natural contractions in the atrium and which, on expiration, triggers a ventricular pacing pulse. It also includes an upper rate timer which defines an upper rate interval initiated in response to sensed ventricular contractions or ventricular pacing pulses. Time-out of the A-V delay timer during this interval causes generation of a ventricular pacing pulse at the expiration of the interval.

The present invention addresses the problem of atrial bradycardia in the context of a VDD pacemaker by providing a selectable post-ventricular atrial refractory period following ventricular pacing pulses. The post-ventricular atrial refractory period (PVARP) is defined by a fourth timing means, which defines the PVARP beginning with a ventricular contraction or a ventricular pacing pulse. During this period, detected atrial contractions are ineffective to start the A-V delay timer. The present invention allows the pacemaker to track naturally occurring high atrial rates, while reducing the chance for responding inappropriately to retrograde P-waves. In response to delivery of a pacing pulse due to expiration of the A-V interval timer, a short post-ventricular atrial refractory period, e.g. 250 ms is selected. In this case, the ventricular pacing pulse, being closely preceded by an atrial contraction, is not likely to induce retrograde conduction. If the ventricular pacing pulse is triggered as a result of the time out of the lower rate timer, a longer post-ventricular atrial refractory period, e.g. 400 ms, is selected. This prevents ventricular pacing pulses not triggered in response to sensed atrial contractions from inducing pacemaker mediated tachycardias.

The present invention also provides a pacemaker which is simple to use and easy for the physician to monitor. Because post-ventricular refractory periods are selected between two preset intervals, and because the selection criteria is based upon events which are readily determinable by the physician, monitoring the EKG strip of the pacemaker allows its proper functioning to be verified. For example, a ventricular pacing pulse following a preceding ventricular pacing pulse by the lower rate (V-V) interval can be presumed to have the long PVARP thereafter, and a pacing pulse preceded by a ventricular pacing pulse or ventricular contraction by less than the lower rate interval will have the short PVARP thereafter, whether or not the atrial contraction is visible on the EKG strip. This can simplify follow-up and monitoring of the pacemaker as compared to some of the prior art pacemakers discussed above employing complex regimes for regulating post-ventricular atrial refractory period, which require diagnostic markers or other telemetry for determination of proper functioning.

The present invention also lends itself to embodiment in relatively simple circuitry. Unlike some of the more complex algorithms for regulating post-ventricular atrial refractory period in the above-cited prior art, the present invention can be readily implemented with simple digital circuitry, and does not require the use of electronic circuitry having arithmatic capabilities, e.g. microprocessors.

The description of the invention herein, and the discussion of the prior art above both relate the functioning of the pacemakers described to the functioning of the heart by specifying the reactions of the pacemakers to contractions of the heart. It should be understood that the pacemakers do not directly sense the physical contractions of the heart, but instead sense the electrical signals indicative of depolarization of the heart tissue, associated with the physical contractions.

DETAILED DESCRIPTION OF THE INVENTION

Figures 1A, 1B:
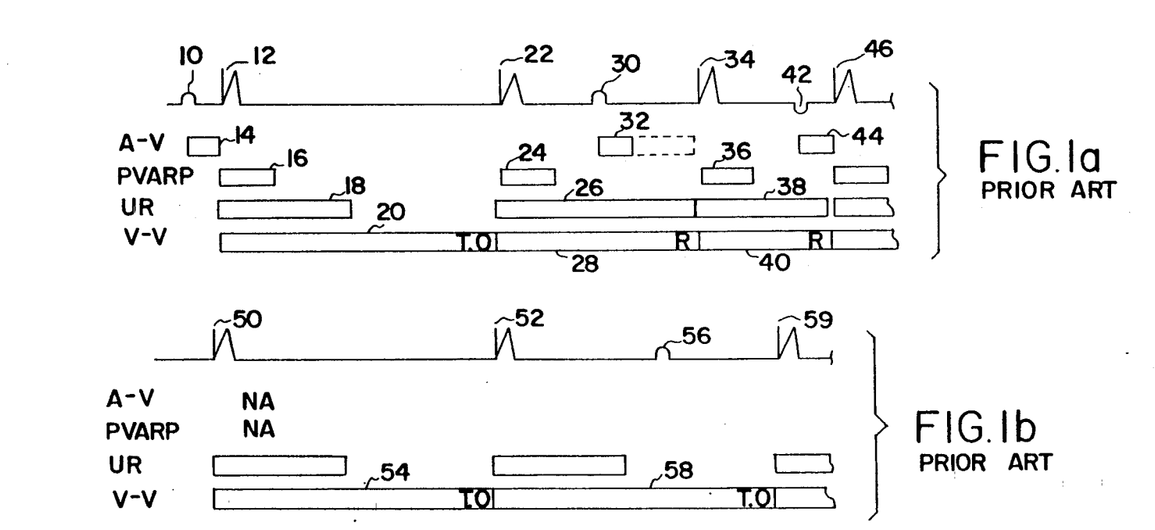
FIG. 1A is a simulated EKG strip illustrating the operation of the pacemaker described in U.S. Pat. No. 4,344,437, discussed above.
FIG. 1B is a simulated EKG strip, illustrating the function of the pacemaker described in U.S. Pat. No. 4,363,325, also discussed above.

FIG. 1A is a simulated EKG tracing simulating the operation of the pacemaker illustrated in U.S. Pat. No.

4,344,437, discussed above. Below the simulated EKG tracing is a timing chart indicating the duration of various intervals timed by the pacemaker including an A-V interval, the post-ventricular atrial refractory period (PVARP), the upper rate interval (UR) and the lower rate (V-V) interval. For purposes of comparison with the device of the present application, the device of the previous application is presumed to be set to display an A-V interval of 100 ms, a post-ventricular atrial refractory period of 250 ms and an upper rate interval switchable between 400 ms (150 bpm) and 600 ms (100 bpm), as set forth in the cited application. While in the cited application the atrial refractory period is not specifically disclosed, reference is made to a previous U.S. Pat. No. 4,343,311, which specifies a post-ventricular atrial refractory period of 170 ms. For purposes of the illustration, it is presumed that the lower rate timer is set to a rate of 70 bpm, corresponding to an 850 ms V-V interval.

The strip begins with a sensed atrial contraction 10, which causes generation of a pacing pulse 12 at the end of the A-V interval 14, 100 ms thereafter. At this time, the post-ventricular atrial refractory period 16 is initiated, along with the upper rate interval 18 and the lower rate (V-V) interval 20. On expiration of the V-V interval 20, a subsequent pacing pulse 22 is generated. The next post-ventricular atrial refractory period 24 is initiated, along with the next upper rate interval 26. Because pacing pulse 22 is generated at expiration of the previous V-V interval, upper rate interval 26 is extended to 600 ms, as disclosed in the above-cited patent. The lower rate timer is also reset to begin timing V-V interval 28.

After the expiration of the post-ventricular atrial refractory period 24, a P-wave 30 is sensed which, because it is after the expiration of post-ventricular atrial refractory period 24, reinitiates the A-V delay timer to time out A-V interval 32. Because upper rate interval 26 has not timed out when A-V interval 32 expires, delivery of ventricular pacing pulse 34 is delayed until the end of upper rate interval 26. Post-ventricular atrial refractory period 36, upper rate interval 38 and lower rate interval 40 are all reinitiated with pacing pulse 34. Because pacing pulse 34 was triggered in response to sensing of an atrial contraction, the upper rate interval 38 returns to 400 ms. At 42, a retrograde P-wave is illustrated. Because of the long separation between atrial contraction 30 and ventricular pacing pulse 34, propagation of a signal from the ventricle, back to the atrium in the form of retrograde P-wave 42 is possible. This is seen as an atrial contraction by the pacemaker, initiating timing of A-V interval 44, and allowing generation of pacing pulse 46 at the expiration of the 400 ms upper rate interval 38. Because the inverted P-wave 42 does not closely precede the ventricular pacing pulse, the possibility remains open for a retrograde P-wave following pacing pulse 46 to restart the A-V interval. If this pattern persists, it may result in a pacemaker mediated tachycardia.

FIG. 1B shows a simulated timing strip from a pacemaker according to above-cited U.S. Pat. No. 4,363,325. In this strip, it is assumed that the pacemaker has changed from atrial synchronous mode (VDD) to ventricular inhibited mode (VVI). As illustrated, ventricular pacing pulses 50 and 52 are separated by the V-V interval 54. The occurrence of a P-wave 56, appropriately timed for causing generation of a ventricular stimulus pulse is ignored, until two atrial contractions (P-waves) at the appropriate rate are detected. Thus, the device continues to pace at 59 at a rate corresponding to the lower rate interval 58. While this system prevents closely spaced ventricular pacing pulses due to atrial bradycardia, it lacks the ability to take advantage of the occasional properly timed atrial contraction to provide an A-V synchronous heartbeat.

Figure 2:
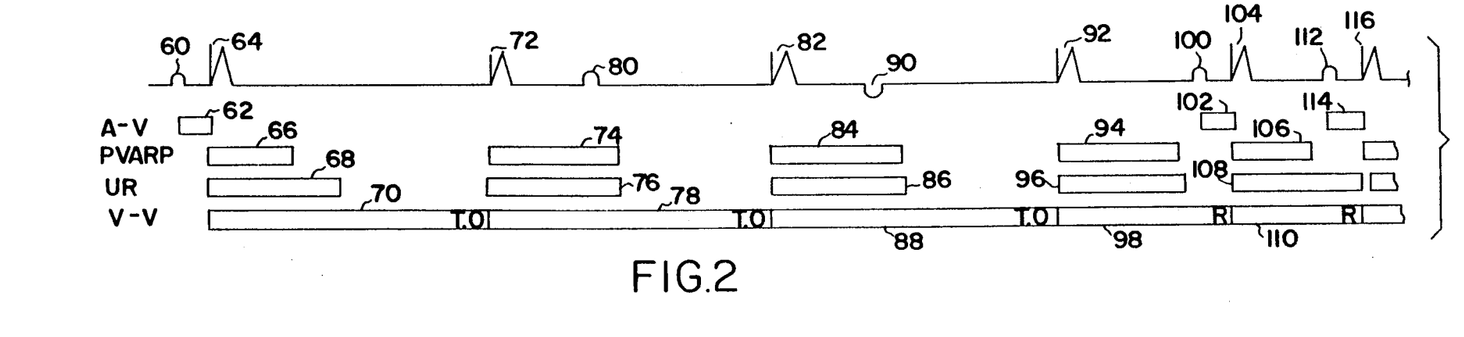
FIG. 2 is a sample EKG strip illustrating the operation of the device of the present application in similar circumstances.

FIG. 2 shows a simulated EKG tracing of a VDD type pacemaker according to the present invention. This tracing illustrates the behavior of a pacemaker according to the present invention in situations corresponding to those illustrated in FIGS. 1A and 1B above. In response to a sensed atrial contraction 60, the 100 ms A-V interval 62 is initiated, followed by generation of a pacing pulse 64. Concurrent with generation of pacing pulse 64, a 250 ms PVARP 66, a 400 ms upper rate interval 68 and an 850 ms V-V interval 70 are initiated. At the expiration of the V-V interval 70, a subsequent ventricular pacing pulse 72 is generated. Because ventricular pacing pulse 72 was generated in response to time out of the lower rate timer (time out of the V-V intervals 70), the post-ventricular atrial refractory period 74 is lengthened to 400 ms. Upper rate interval 76 and the V-V interval 78 are initiated concurrent with ventricular pacing pulse 72. A bradycardic P-wave 80 occurs, separated from pacing pulse 72 by a time period in excess of PVARP 66, following atrial synchronous pacing pulse 64. The extension of PVARP 74 to 400 ms prevents resynchronization of the pacemaker with the bradycardic P-wave and avoids closely spaced ventricular pacing pulses. At the expiration of V-V interval 78, the pacing pulse 82 is generated. Again, because this pacing pulse occurs following time out of the V-V interval 78, PVARP 84 is extended to 400 ms. Upper rate interval 86 and V-V interval 88 are reinitiated concurrent with pacing pulse 82. In this case, the ventricular contraction initiated by pacing pulse 82 causes propagation in a reverse direction up the conduction path, causing the occurrence of retrograde P-wave 90, illustrated as occurring more than 250 ms following pacing pulse 82. Because the post-ventricular atrial refractory period 84 has been extended, P-wave 90 is ineffective to initiate timing of an A-V interval. As such, pacemaker mediated tachycardia is avoided.

At the expiration of V-V interval 88, pacing pulse 92 is generated, initiating post-ventricular atrial refractory period 94, upper rate interval 96 and V-V interval 98. After the expiration of post-ventricular atrial refractory period 94, a P-wave 100 occurs, appropriately timed for causing generation of a ventricular pacing pulse. Because P-wave 100 occurs after the expiration of the post-ventricular atrial refractory period 94, it is effective to initiate timing of an A-V interval 102, and to cause generation of a ventricular pacing pulse 104, 100 ms thereafter. Thus, unlike the pacemaker described in the above-cited Roline et al patent, the pacemaker of the present invention can take advantage of an appropriately timed atrial contraction to provide atrial synchronous pacing.

Because pacing pulse 104 was generated in response to sensing in the atrium, the subsequent PVARP 106 is reduced to 250 ms. Upper rate interval 108 and V-V interval 110 are also initiated.

P-wave 112, representing a high natural sinus rate, occurs more than 250 ms, but less than 400 ms following pacing pulse 104. Because the previous ventricular pacing pulse was an atrial synchronous pulse, it is reasonable to assume that P-wave 112 is not a retrograde P- wave, and thus is appropriate for triggering ventricular stimulation. The reduction of post-ventricular atrial refractory period 106 to 250 ms from 400 ms allows A-V interval 114 to be started in response to the sensing of atrial contraction 112, causing generation of ventricular pacing pulse 116 at the later of the expiration of A-V interval 114 or upper rate interval 108. This allows the pacemaker to track natural atrial rates up to 150 bpm, which would not be possible when employing a fixed post-ventricular atrial refractory period of 400 ms.

As illustrated, the present invention provides the ability to track the atrium at high rates, while avoiding the problem of closely spaced ventricular pacing pulses common to VDD pacemakers and reducing the potential for a pacemaker mediated tachycardia. In addition to the improved behavior of the pacemaker, the behavior is also extremely easy to understand and to follow using just the EKG strip. The physician reviewing the strip typically employs a measuring caliper to determine spacing of ventricular pacing pulses. While this measurement is not highly accurate, it will be of substantial assistance in allowing the physician to determine whether the pacemaker is correctly responding to atrial contractions. For example, if an atrial contraction is visible on the EKG within 400 ms of a ventricular pacing pulse, a physician can measure the interval between the pacing pulse and the immediately preceding pacing pulse. If the measured interval approximates the lower rate interval, the physician will not expect the atrial contraction to be sensed. If the measured interval is substantially less than the lower rate interval, the physician will expect the atrial pulse to be sensed unless it occurs within 250 ms of the ventricular pacing pulse. This feature is believed to be particularly advantageous in the case of a physician who may not have a pacemaker programmer available which is compatible with the implanted device, and thus cannot make use of transmissions of diagnostic markers or other pacemaker based telemetry. In order to simplify EKG analysis, it is suggested that this present invention may best be employed in a pacemaker of the type in which the pacemaker reverts to ventricular asynchronous pacing at the programmed rate upon application of a magnet. This will allow the physician to readily determine the lower rate interval for subsequent diagnostic use.

Figure 3A:
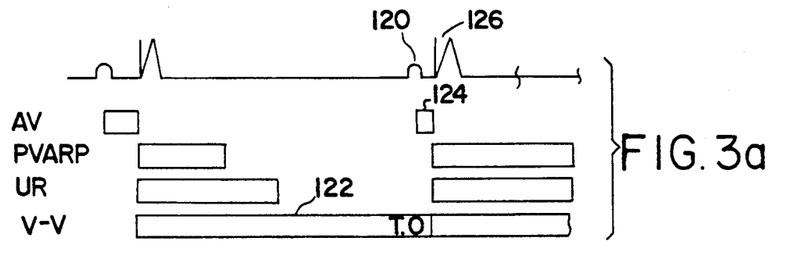
FIGS. 3A, 3B and 3C all illustrate variations in operation of a pacemaker according to the present invention.
Figure 3B:
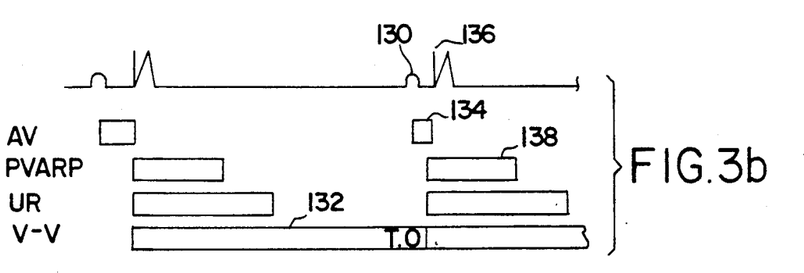
Figure 3C:
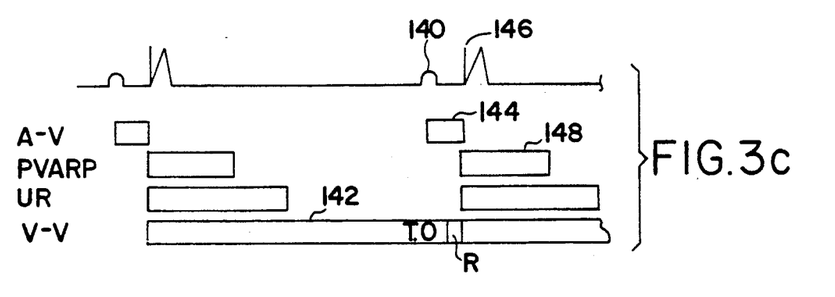

FIGS. 3A, 3B and 3C illustrate alternative approaches to dealing with a situation unique to VDD pacemakers, and illustrate possible applications of the present invention with regard to this situation. In a VDD pacemaker, unlike a DDD pacemaker, provision is made for generating a ventricular pacing pulse in the absence of a preceding atrial contraction. Because there is no atrial pulse generator, it is possible for an atrial contraction to occur slightly before a scheduled ventricular pacing pulse. For example, if the A-V interval is 100 ms, an atrial contraction may occur 50 ms prior to expiration of the V-V interval. FIGS. 3A, 3B and 3C illustrate alternative ways of dealing with this occurrence, in the context of the present invention.

FIG. 3A illustrates a P-wave 120 occurring approximately 50 ms prior to the expiration of V-V interval 122. In this case, it initiates timing of the A-V interval 124. However, expiration of the V-V interval 122 terminates timing of the A-V interval 124 and causes generation of a ventricular pacing pulse 126. In this embodiment of the invention, the PVARP 128 is extended to 400 ms based on the criteria that the pacing pulse 126 was not triggered in response to expiration of the A-V interval, but instead by expiration of the V-V interval.

FIG. 3B illustrates a similar situation. In this case, p-wave 130 occurs 50 ms prior to expiration of V-V interval 132. This initiates timing of A-V interval 134, which again is cut short by the expiration of A-V interval 132, causing generation of ventricular pacing pulse 136. In this case, however, the subsequent post-ventricular atrial refractory period 138 is allowed to remain at 250 ms. Because pacing pulse 136 was in fact preceded by an atrial contraction, the possibility of retrograde conduction leading to pacemaker mediated tachycardia is avoided, and the PVARP need not be extended. However, this behavior is not as readily determined by the physician, especially in situations in which the atrial contraction 130 closely precedes or to some extent overlaps with the paced ventricular beat. However, this embodiment of the invention still accomplishes the goals of avoiding inappropriately closely coupled ventricular pacing pulses in VDD pacing mode and avoidance of pacemaker mediated tachycardia.

FIG. 3C illustrates yet another embodiment of the present invention. In this tracing, P-wave 140 also occurs 50 ms prior to the expiration of V-V interval 142. In this case, however, A-V interval 144 is allowed to time out, causing generation of a pacing pulse 146 100 ms thereafter. Because this pacing pulse 146 meets both basic criteria for reducing the post-ventricular atrial refractory period, i.e. preceded by an atrial contraction and generated in response to time out of the A-V interval, the post-ventricular atrial refractory period 148 is set at 250 ms. This behavior mode, while maximizing the possibility for appropriate atrial synchronous pacing, will be somewhat harder for the physician to monitor absent diagnostic markers, as it may be difficult to determine the occurrence of P-wave 140 on a surface EKG and, if P-wave 140 occurs close to one A-V delay prior to the expiration of V-V interval 142, it may be difficult to determine which time interval triggered the pacing pulse, and thus what the following post-ventricular atrial refractory period might be. Nonetheless, the present invention can be used either with a pacemaker of the type illustrated in FIGS. 3A and 3B which does not affect timing of the ventricular pacing pulse in response to an atrial contraction occurring less than one A-V delay prior to the expiration of the V-V interval, or with a pacemaker as illustrated in FIG. 3C, which does alter the timing of the ventricular pacing pulse in such situations.

Figure 4A:
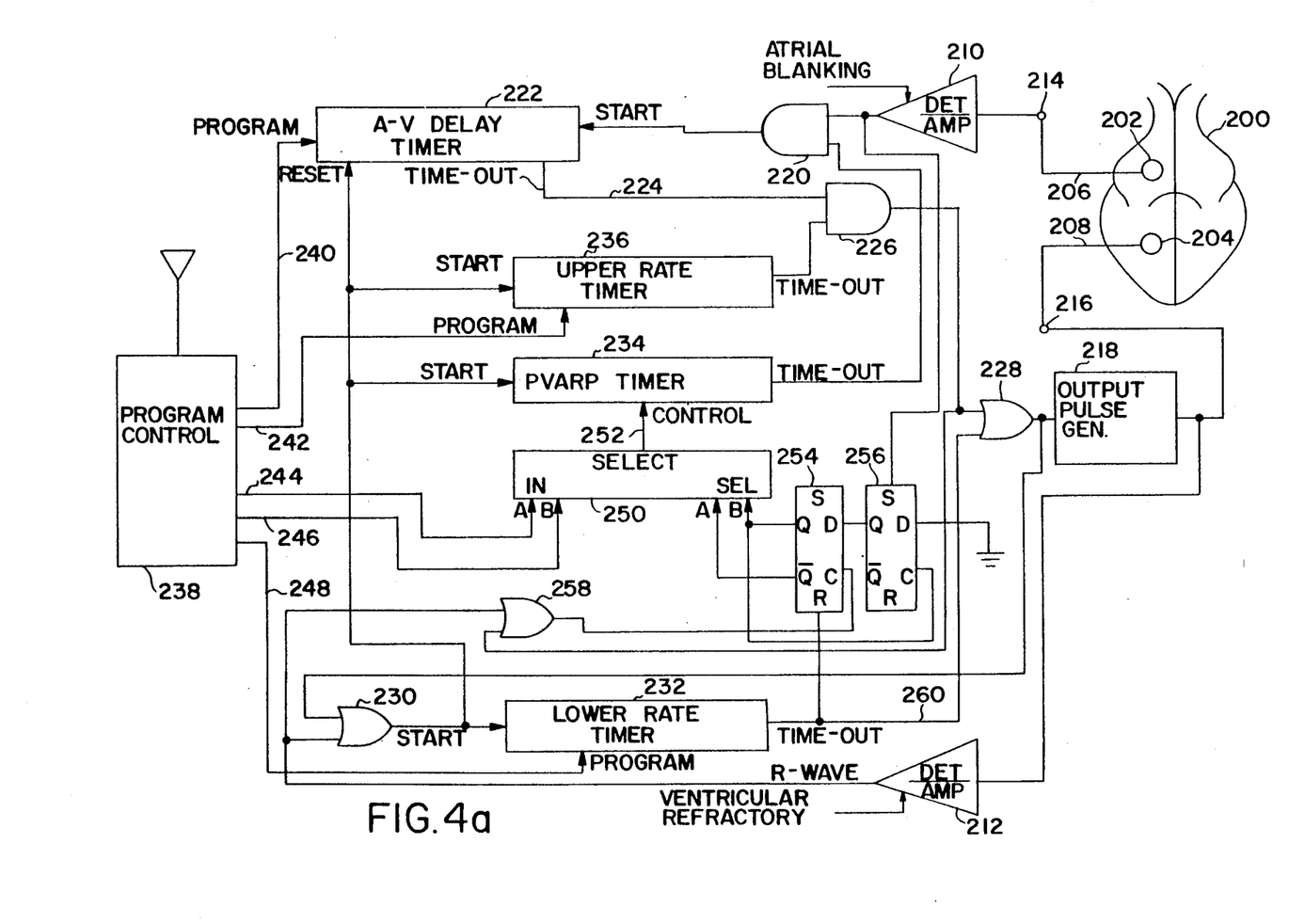
FIGS. 4A, 4B and 4C are functional block diagrams illustrating three embodiments of pacemakers according to the present invention.
Figure 4B:
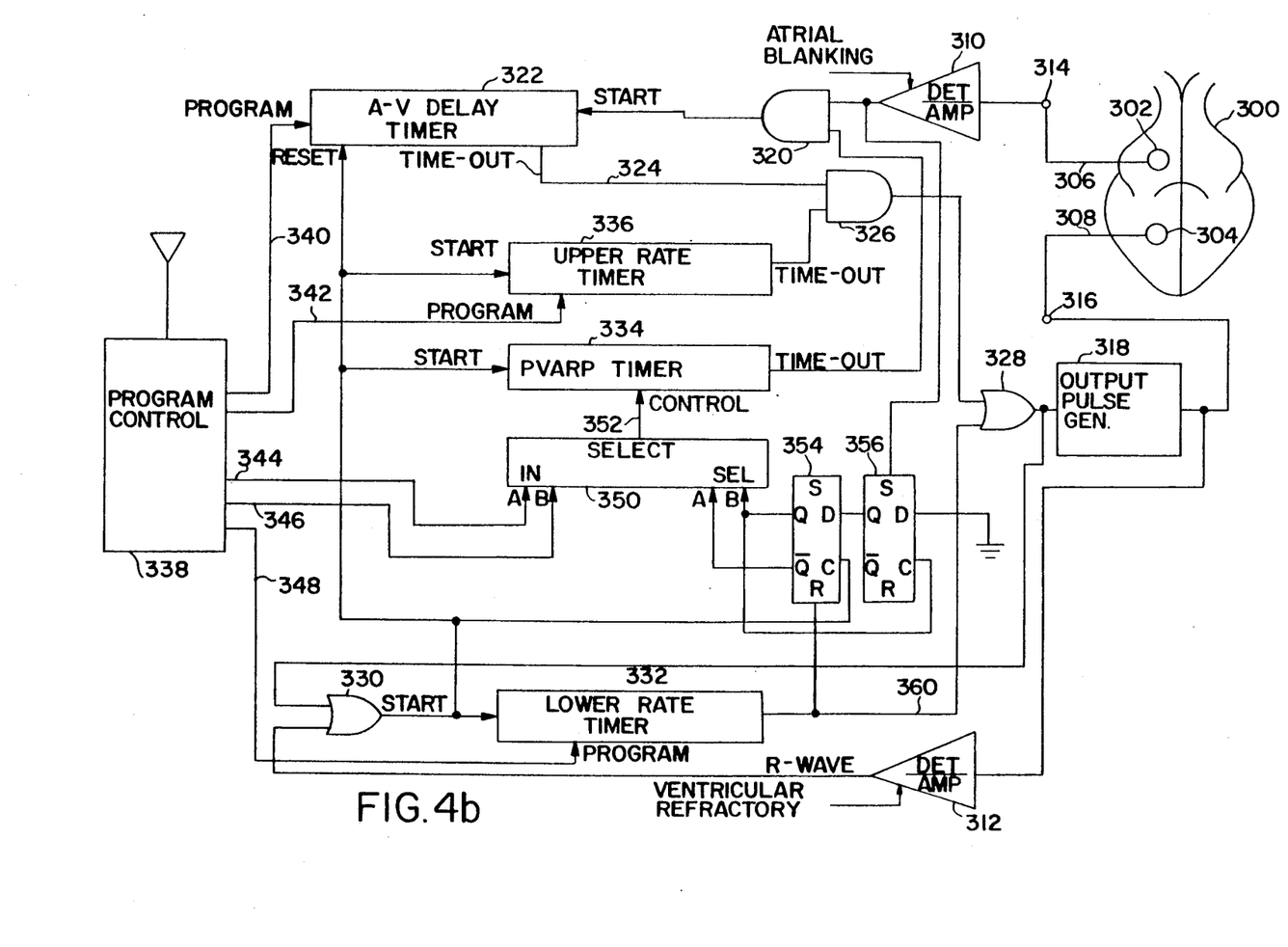
Figure 4C:
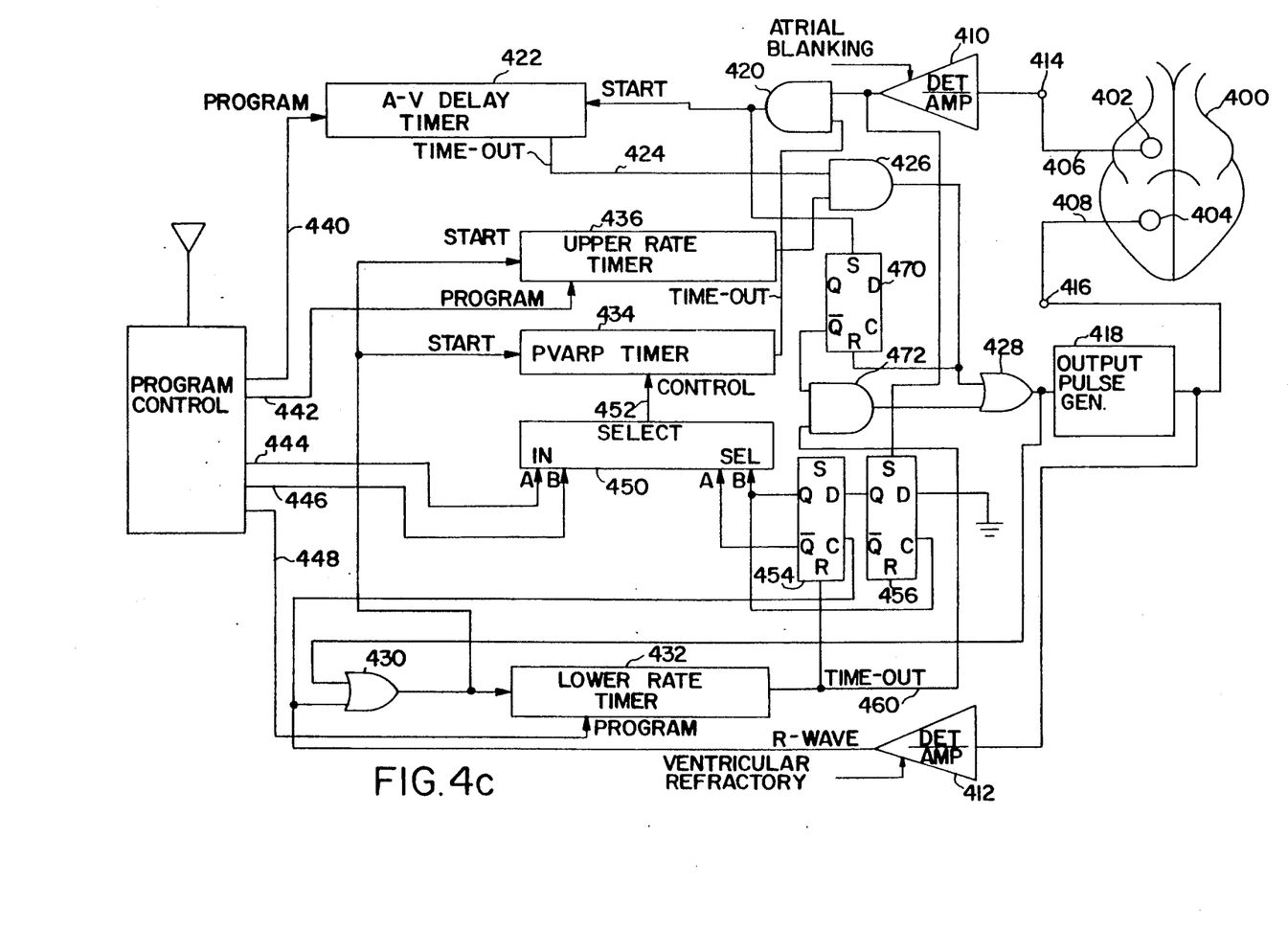

FIGS. 4A, 4B and 4C illustrate functional block diagrams of three embodiments of the present invention. The illustrative EKG of FIG. 2 applies to all three embodiments. The illustrative EKG's of FIGS. 3A, 3B and 3C apply to FIGS. 4A, 4B and 4C, respectively. In FIGS. 4A, 4B and 4C, corresponding structure is illustrated with corresponding numbers. For example, structure 400 in FIG. 4C corresponds to structure 300 in FIG. 4B and corresponds to structure 200 in FIG. 4A. FIG. 4A will be described in some detail. FIGS. 4B and 4C will be described in detail only in so far as it is necessary to describe the difference in operation between the embodiments illustrated therein and that of FIG. 4A. Operation of functional elements illustrated in FIGS. 4B and 4C corresponding to those in 4A, not otherwise discussed, can be presumed to be the same as discussed in FIG. 4A.

FIGS. 4A, 4B and 4C are drawn to illustrate a pacemaker having the same basic functional organization as pacemakers illustrated in above-cited Greatbatch and Adams patents. These schematics are intended to be illustrative of the function of the pacemaker, but should not be construed as limiting with regard to the appropriate circuitry implementation. The pacemaker according to the present invention may readily be accomplished by means of discrete analog circuitry, integrated digital circuitry, or utilizing microprocessor technology.

FIG. 4A illustrates a first embodiment of a pacemaker according to the present invention. The pacemaker is coupled to a human heart 200 by means of an atrial electrode 202 and a ventricular electrode 204 mounted to atrial and ventricular leads 206 and 208, respectively. Leads 206 and 208 are coupled to atrial sense amplifier 210 and ventricular sense amplifier 212 by means of electrical connectors 214 and 216. Ventricular pacing lead 208 and electrode 204 are also coupled to ventricular output pulse generator 218. Atrial contractions are sensed by means of electrode 202, amplified and detected by amplifier 210, passed through logic gate 220 and used to initiate timing of the A-V interval by A-V delay timer 222. A-V delay timer functions as a nonresettable one-shot, and cannot be restarted during timing of the A-V interval. On time out of the A-V delay interval, a signal on line 224 is generated, which is in turn passed through logic AND 226 and OR gate 228 to trigger output pulse generator 218 to generate a ventricular stimulation pulse which is applied to ventricular electrode 204.

Ventricular contractions are sensed by electrode 204, amplified and detected by amplifier 212 and passed through OR gate 230 to restart the lower rate timer 232, along with the post-ventricular atrial refractory period timer 234, and the upper rate timer 236. Triggering of a ventricular pacing pulse via OR gate 228 also serves to restart lower rate timer 232, PVARP timer 234 and upper rate timer 236 via OR gate 230. PVARP timer 234 and lower rate timer 232 function as resettable oneshots, and can be restarted during timing of the V-A and V-V intervals. The output of OR gate 230 is also used to reset A-V delay timer 222, interrupting timing of an A-V delay interval, if underway.

Initiation of A-V delay timer 222 to time out the A-V interval is dependent upon the time out of PVARP timer 234, which enables the amplified and detected atrial contraction to pass through AND gate 220 and initiate the A-V delay timer 222. Triggering of a ventricular pacing pulse due to time out of the A-V interval is dependent upon time out of the upper rate interval determined by upper rate timer 236. Only after both the A-V delay timer 222 and the upper rate timer 236 have timed out is a signal passed through AND gate 226, and then through OR gate 228 to initiate generation of a ventricular pacing pulse by output pulse generator 218. This also provides the Psuedo-Wenkebach behavior discussed above in conjunction with the above-cited Adams patent.

If a signal from AND gate 226 does not precede time out of lower rate timer 232, on expiration of the V-V interval, lower rate timer 232 will trigger output pulse generator 218 via OR gate 228 to pace the ventricle. This will also result in resetting of the lower rate timer 232, the PVARP timer 234, and the upper rate timer 236, as well as disabling timing of the A-V interval by the A-V delay timer 222, if then underway.

PVARP timer 234, like A-V delay timer 222, upper rate timer 236 and lower rate timer 232 are digital timers having selectable time periods. For example, they may be jam-in down counters, with the number with which they are loaded being determined by the program control logic 238 which defines numbers of counts corresponding to the specified time intervals by means of multibit data buses 240, 242, 244, 246 and 248. In the case of PVARP timer 234, selection between two available intervals found on buses 244 and 246 is made by means of select logic 250 which provides the selected PVARP interval to PVARP timer 234 by means of a multibit data bus 252.

Selection between the values on bus 244 and bus 246 is accomplished by means of flip-flops 254 and 256, which keep track of which of the A-V delay timer 222 and the lower rate timer 232 initiated generation of a ventricular pacing pulse. In response to detection of an atrial contraction by atrial amplifier 210, flip-flop 256 is set, driving its Q output high. On the next subsequent ventricular contraction sensed by amplifier 212, flipflop 254 is clocked via OR gate 258 to pass through the logic state on the Q output of flip-flop 256 to select line 260. If select line 260 goes from low to high, indicating the occurrence of an atrial contraction prior to the sensed ventricular contraction, this in turn will clock flip-flop 256, setting the Q output low. However, flipflop 254 will remain set with its Q output high, and its not Q output on line 262 low. In this case, the number of counts corresponding to a 400 ms post-ventricular atrial refractory period on data bus 246 is passed through select logic 250 to PVARP timer 234. The same series of events occurs in response to a ventricular pacing pulse triggered by means of a signal from AND gate 226 which is also passed through OR gate 258.

If, on the other hand, a ventricular pacing pulse is generated due to expiration of the V-V interval determined by lower rate timer 234, a signal on line 260 is used to both trigger the pacing pulse via OR gate 228 and to reset flip-flop 254, setting its Q output low and its not Q output high. This in turn selects the number on data bus 244 corresponding to a 250 ms post-ventricular atrial refractory period to be passed through select logic 250 to PVARP timer 234.

The values given in the above description and in conjunction with the simulated EKG's in FIGS. 2, 3A, 3B and 3C above are intended to be examples of appropriate time intervals which may be selected. Other time intervals may be selected through program control logic 238. However, it is important in order for the invention to function in its optimum fashion that the upper rate interval determined by upper rate timer 236 should not be substantially greater than the sum of the shorter post-ventricular atrial refractory period and the A-V delay. This will allow appropriately timed bradycardic atrial contractions to cause generation of a closely coupled ventricular pacing pulse, as illustrated in the simulated EKG in FIG. 2.

FIG. 4B illustrates a pacemaker corresponding generally to that illustrated in 4A modified so that its operation corresponds to that illustrated in FIG. 3B. In this case, flip-flop 354, corresponding to flip-flop 254 in FIG. 4A is clocked in response to each sensed ventricular contraction and each ventricular pacing pulse, via OR gate 330. The result of this change is that for pacing pulses initiated in response to time out of the lower rate timer 332, but preceded by an atrial contraction as illustrated in FIG. 3B, select logic 350 will select the number on data bus 344, corresponding to the 250 ms atrial refractory period. Otherwise, all remaining structure is illustrated and operates identically to corresponding structure illustrated in FIG. 4A.

FIG. 4C illustrates a third embodiment of a pacemaker corresponding generally to that illustrated in FIG. 4A, but modified so that its operation corresponds to FIG. 3C. In this embodiment, the occurrence of an atrial contraction after the expiration of the post-ventricular atrial refractory period, results in a signal from AND gate 420 which is used to set flip-flop 470, disabling the signal due to time out of the V-V interval by lower rate timer 432 from passing through AND gate 472 and triggering a ventricular pacing pulse. Instead, the A-V delay timer 422 will time out, and trigger a ventricular pacing pulse via AND gate 426 and OR gate 428, as illustrated in FIG. 3C.

Selection of the appropriate post-ventricular atrial refractory in FIG. 4C is accomplished somewhat differently than illustrated in FIG. 4A, in that flip-flop 454 is clocked in response to the occurrence of a sensed natural atrial ventricular contraction or in response to a signal from OR gate 428 indicating the occurrence of a ventricular pacing pulse, via OR gate 430. However, if an A-V interval is being timed out by A-V delay timer 422, time out of the lower rate timer 432 will not initiate a pacing pulse. Following a non-refractory sensed atrial contraction, flip-flop 470 is set by AND gate 420, disabling the time-out signal on line 460 from passing through AND gate 472 to trigger a pacing pulse. On time out of the A-V interval, flip-flop 470 is reset. This results in operation as illustrated in FIG. 3C., above. The embodiment illustrated in FIG. 4C in this respect is a hybrid of the embodiments illustrated in FIGS. 4A and 4B. Each pacing pulse triggered by time out of the lower rate timer 432 results in selection of the long post-ventricular atrial refractory period, each pacing pulse following time out of the A-V interval results in the selection of the shorter post-ventricular atrial refractory period.

The above embodiments are intended to illustrate various types of VDD pacemakers in which the present invention could be employed. While the present invention represents a departure from the inventions set forth in the above-cited U.S. Pat. No. 4,344,437, it is anticipated that the invention might also be used in conjunction with certain features of the pacemaker disclosed in this patent. For example, the selectable post-ventricular atrial refractory period might be used in conjunction with a selectable upper rate interval. In such an embodiment, select logic corresponding to select logic 250 illustrated in FIG. 4A would select between counts corresponding to different upper rate intervals, in response to the outputs of flip-flop 254 (FIG. 4A). When the post-ventricular atrial refractory period is reduced in response to the generation of an atrial synchronous pacing pulse, it might, in some cases, be appropriate at the same time to reduce the upper rate interval to facilitate following more rapid natural atrial rhythms. For example, if the reduced duration post-ventricular atrial refractory period were to be 250 ms, it might also be appropriate to reduce the ventricular upper rate interval from 400 to 350 ms, to allow tracking of natural atrial rates in excess of 150 bpm.

As such, the above embodiments should be considered exemplary, rather than limiting, with respect to the following claims.

In conjunction with the above specification, I claim:

1. A pacemaker comprising:

atrial amplifier means for sensing contractions of the atrium;

ventricular amplifier means for sensing contractions of the ventricle;

ventricular pulse generator means for providing ventricular pacing pulses;

A-V delay means for timing A-V intervals initiated in response to sensing of atrial contractions by said atrial amplifier means and for triggering said ventricular pulse generator means to provide said ventricular pacing pulses at the expiration of said A-V intervals;

lower rate timer means for defining V-V intervals initiated in response to sensing of ventricular contractions by said ventricular amplifier means or in response to provision of said ventricular pacing pulses by said ventricular pulse generator means and for triggering said ventricular pulse generator means to provide said ventricular pacing pulses at the expiration of said V-V intervals;

refractory timer means for timing PVARP intervals initiated in response to provision of said ventricular pacing pulses by said ventricular pulse generator means, and for preventing the sensing of atrial contractions by said atrial amplifier means from initiating timing of said A-V interval during said PVARP intervals; and control means coupled to said refractory timer means for controlling the duration of said PVARP interval, said control means comprising means for defining predetermined first and second PVARP interval durations, said first PVARP interval duration being longer than said second PVARP interval duration; and wherein said atrial amplifier means comprises means for sensing atrial contractions throughout the time periods between expirations of said PVARP intervals and expirations of said V-V intervals and wherein said control means further comprises means responsive to atrial contractions sensed by said atrial amplifier means during said time periods between the expirations of said PVARP intervals and the expirations of said V-V intervals, for selecting between said first and second PVARP interval durations such that said first PVARP interval duration is selected only following generation of said ventricular pacing pulses triggered by the expiration of said V-V intervals and not preceded by the sensing of atrial contractions by said atrial sensing amplifier means outside of said PVARP intervals, during the said V-V intervals.

2. A pacemaker according to claim 1 wherein said pacemaker further comprises means for preventing expiration of said V-V intervals from triggering said ventricular pulse generator means to provide ventricular pacing pulses during timing of said A-V intervals by said A-V delay means.

3. A pacemaker according to claim 1 or claim 2 further comprising upper rate timing means for timing an upper rate interval initiated in response to generation of a ventricular pacing pulse and for preventing generation of a ventricular pacing pulse due to expiration of said A-V interval during said upper rate interval.

4. A pacemaker according to claim 3 wherein the duration of said upper rate interval is approximately equal or less than the sum of the durations of said A-V and first PVARP intervals.

5. A cardiac pacemaker, comprising:

atrial amplifier means for sensing electrical signals indicative of contractions of the atrium;

ventricular amplifier means for sensing signals indicative of contractions of the ventricle;

ventricular pulse generator means for providing ventricular pacing pulses;

A-V delay timer means for defining A-V intervals initiated in response to sensing of said signals indicative of atrial contractions by said atrial amplifier means and for triggering said ventricular pulse generator means to provide said ventricular pacing pulses at the expirations of said A-V intervals;

lower rate timer means for defining V-V intervals initiated in response to sensing of said signals indicative of ventricular contractions by said ventricular amplifier means or in response to provision of said ventricular pacing pulses by said ventricular pulse generator means and for triggering said ventricular pulse generator means to provide said ventricular pacing pulses at the expiration of said V-V intervals, wherein said pulse generator means generates said pacing pulses responsive to the first to expire of said A-V and V-V intervals;

refractory timer means for defining PVARP intervals initiated in response to provision of aid ventricular pacing pulses by said ventricular pulse generator means and for preventing the sensing of said electrical signals indicative of atrial contractions by said atrial amplifier means during said PVARP intervals from initiating timing of said A-V intervals; and control means coupled to said refractory timer means for defining first and second PVARP interval durations to be timed by said refractory timer means, said first PVARP interval duration being longer than said second PVARP interval duration; and wherein said atrial amplifier means comprises means for sensing electrical signals indicative of atrial contractions throughout the time periods between expirations of said PVARP intervals and expirations of said V-V intervals and wherein said control means further comprises selector means for selecting said first PVARP interval duration only when a said ventricular pacing pulse is generated at the expiration of a said V-V interval during which an electrical signal indicative of an atrial contraction is not sensed by said atrial sense amplifier means outside of a said PVARP interval, and for selecting said second PVARP interval duration when ever a said ventricular pacing pulse is generated at the expiration of a said V-V interval during which an electrical signal indicative of an atrial contraction is sensed by said atrial sense amplifier means outside of a said PVARP interval.

6. A cardiac pacemaker, comprising:

atrial amplifier means for sensing electrical signals indicative of contractions of the atrium;

ventricular amplifier means for sensing electrical signals indicative of contractions of the ventricle;

ventricular pulse generator means for providing ventricular pacing pulses;

A-V delay timer means for defining A-V intervals initiated in response to sensing of said electrical signals indicative of atrial contractions by said atrial amplifier means and for triggering said ventricular pulse generator means at the expiration of the said A-V intervals to provide said ventricular pacing pulses;

lower rate timer means for defining V-V intervals initiated in response to sensing of said electrical signals indicative of ventricular contractions by said ventricular amplifier and in response to the provision of said ventricular pacing pulses by said ventricular pulse generator means and for triggering said ventricular pulse generator means to provide said ventricular pacing pulses at the expiration of said V-V intervals;

refractory timer means defining PVARP intervals initiated in response to provision of said ventricular pacing pulses by said ventricular pulse generator and for preventing sensing of said electrical signals indicative of atrial contractions by said atrial amplifier means during said PVARP intervals from initiating timing of said A-V intervals; and control means coupled to said refractory timer means for defining predetermined first and second PVARP interval durations, said first PVARP interval duration being longer than said second PVARP interval duration; and wherein said atrial amplifier means comprises means for sensing electrical signals indicative of atrial contractions throughout the time periods between expirations of said PVARP intervals and expirations of said V-V intervals and wherein said control means further comprises selector means for selecting said first PVARP interval duration only in response to generation of a said ventricular pacing pulse triggered by expiration of a said V-V interval during which an electrical signal indicative of an atrial contraction is not sensed by said atrial sense amplifier means outside of a said PVARP interval, and for selecting said second PVARP interval duration in response to generation of ventricular pacing pulses triggered by the expiration of said A-V intervals; and inhibit means coupled to said A-V interval and said V-V interval timer means for preventing triggering of said ventricular pacing pulses at the expiration of said V-V intervals during timing of said A-V intervals by said A-V timer means.

7. A pacemaker according to claim 5 or claim 6 further comprising an upper rate timer means for defining an upper rate interval initiated in response to generation of a ventricular pacing pulse and for preventing triggering of a said ventricular pacing pulse due to expiration of said A-V interval during said upper rate interval.

* * * * *